United States Patent
Tanaka et al.

(10) Patent No.: US 6,740,729 B1
(45) Date of Patent: May 25, 2004

(54) PROCESS FOR PRODUCING POLYCARBONATE

(75) Inventors: Shuji Tanaka, Yamaguchi (JP); Shinichi Yoshida, Yamaguchi (JP); Tamiko Nishihira, Yamaguchi (JP)

(73) Assignee: Ube Industries, Ltd., Yamaguchi (JP)

( * ) Notice: Subject to any disclaimer, the term of this patent is extended or adjusted under 35 U.S.C. 154(b) by 0 days.

(21) Appl. No.: 09/674,725

(22) PCT Filed: Mar. 3, 2000

(86) PCT No.: PCT/JP00/01279

§ 371 (c)(1), (2), (4) Date: Jun. 6, 2001

(87) PCT Pub. No.: WO00/52077

PCT Pub. Date: Sep. 8, 2000

(30) Foreign Application Priority Data

Mar. 3, 1999 (JP) .......................................... 11-054936

(51) Int. Cl.$^7$ ............................................. C08G 64/00
(52) U.S. Cl. ........................ 528/196; 526/64; 526/67; 528/198
(58) Field of Search ..................... 526/64, 67; 528/196, 528/198

(56) References Cited

FOREIGN PATENT DOCUMENTS

EP 0832910 * 9/1997

* cited by examiner

Primary Examiner—Terressa Boykin
(74) Attorney, Agent, or Firm—Reed Smith LLP

(57) ABSTRACT

A process for preparing polycarbonate is composed of the steps of transesterifying a dialkyl oxalate and a phenolic compound to give a diaryl oxalate; decarbonylating the diaryl oxalate to give a diaryl carbonate; reacting the diaryl carbonate with a polyvalent hydroxyl compound in the presence of a catalyst containing an amine compound or an ammonium compound to give the polycarbonate, removing a phenolic by-product/amine by-product mixture; collecting the mixture; purifying the mixture so that the amount of the amine by-product in the mixture is reduced to give a phenolic by-product mixture not containing the amine by-product in an amount of more than 600 ppm; and, utilizing thus purified phenolic mixture as a whole or a part of the phenolic compound in the first step.

12 Claims, 1 Drawing Sheet

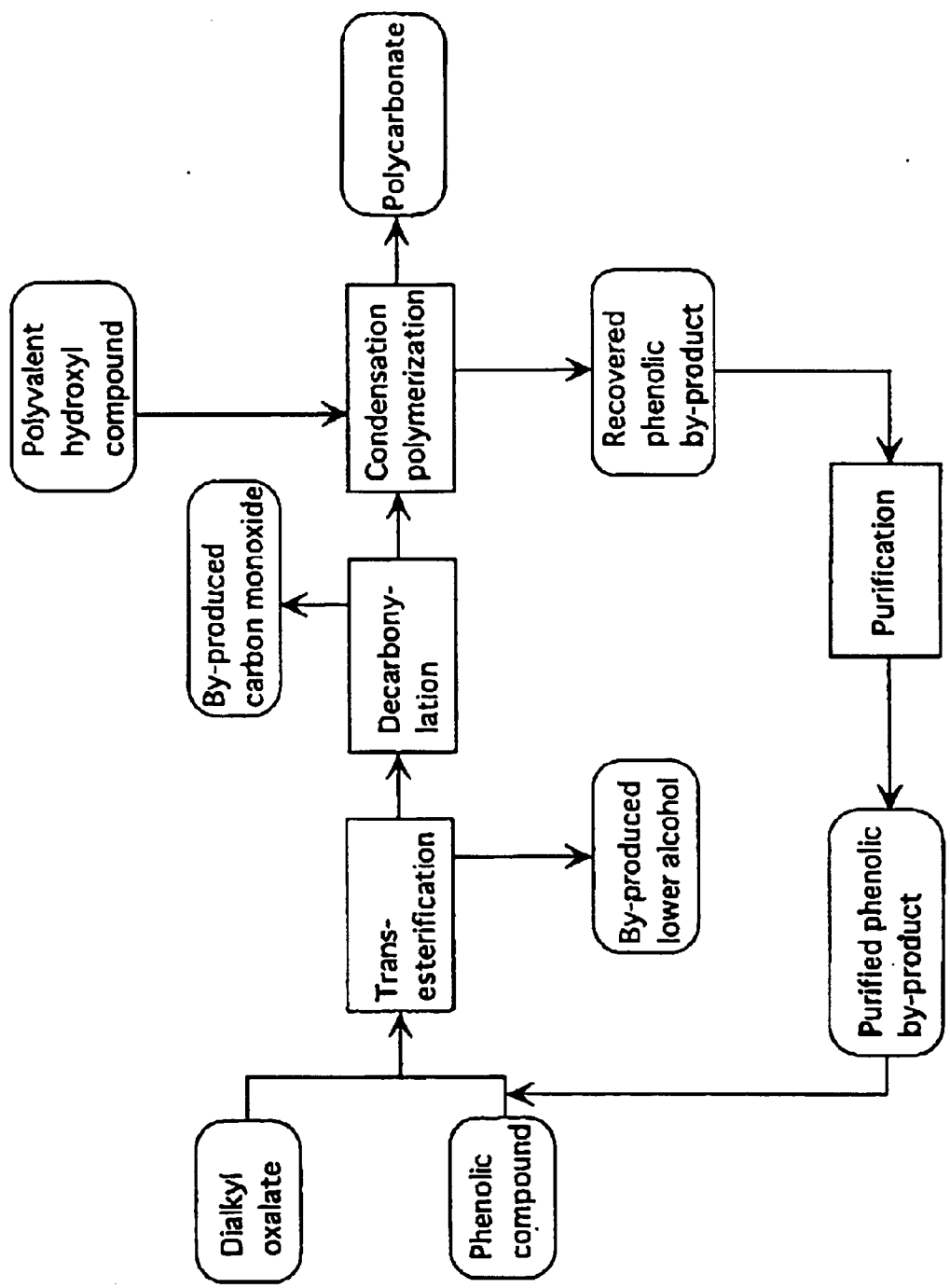
FIGURE

PROCESS FOR PRODUCING POLYCARBONATE

FIELD OF THE INVENTION

The present invention relates to a process for preparing a polycarbonate from a dialkyl oxalate and a phenolic compound.

BACKGROUND OF THE INVENTION

A process for preparing a polycarbonate from a dialkyl oxalate and a phenolic compound which comprises a first step of transesterifying the starting compound to produce a diaryl oxalate, a second step of decarbonylating the resulting diaryl oxalate to produce a diaryl carbonate, and a third step of subjecting the diaryl carbonate to condensation-polymerization reaction with a polyvalent hydroxyl compound to produce a polycarbonate is described in Japanese Patent Provisional Publication No. 10-152552. The Publication 10-152552 further describes such procedure that a phenolic by-product produced in the condensation-polymerization reaction is recovered and recycled to employ as the phenolic compound in the first step.

In the above-mentioned process, the diaryl carbonate of a high purity can be produced using no troublesome phosgene. Therefore, the diaryl carbonate produced from a dialkyl oxalate and a phenolic compound is favorably employed to react with a polyvalent hydroxyl compound to give a polycarbonate having high quality such as high transparency through condensation-polymerization reaction.

It is also known that a catalyst containing tetramethylammonium hydroxide, tetrabutylammnium hydroxide, or tributylamine is employed as a catalyst for performing a condensation-polymerization reaction for the preparation of a polycarbonate from a diaryl carbonate such as diphenyl carbonate and a polyvalent hydroxyl compound such as bisphenol A.

It has been discovered that a portion of the above-mentioned condensation-polymerization catalyst decomposes at an elevated temperature to produce an amine compound (by-product) such as trimethylamine or tributylamine. The amine by-product is migrated into the recovered phenolic by-product.

According to the further study of the investors, in the case that the phenolic by-product is employed as the phenolic compound in the preparation of the diaryl oxalate, the amine by-product in the phenolic by-product gives adverse effects (e.g., deactivation of the catalyst employed) to the reactions in the steps of transesterification and decarbonylation if the amount of the amine by-product in the phenolic by-product increases.

It has been further discovered that the phenolic by-product recovered in the condensation polymerization reaction is sometimes contaminated with an ethereal real by-product. The ethereal by-product in the phenolic by-product sometimes gives such disadvantageous effects as to disturb recovery of reactants and/or reaction product from the reaction system, if the amount of the ethereal by-product in the phenolic by-product increases.

SUMMARY OF THE INVENTION

The present invention resides in a process for preparing paring polycarbonate which comprises the steps of:
  subjecting a dialkyl oxalate and a phenolic compound to transesterification to give a diaryl oxalate;
  subjecting the diaryl oxalate to decarbonylation to give a diaryl carbonate;
  reacting the diaryl carbonate with a polyvalent hydroxyl compound in the presence of a catalyst containing an amine compound or an ammonium compound to give the polycarbonate, removing a mixture containing a phenolic by-product and an amine by-product;
  collecting the mixture;
  purifying the mixture so that the amount of the amine by-product in the mixture is reduced to give a phenolic by-product mixture not containing the amine by-product in an amount of more than 600 ppm; and
  utilizing thus purified phenolic by-product mixture as a whole fir a part of the phenolic compound give the first step.

In the above-mentioned process, if the collected mixture further contains an ethereal by-product, the mixture is preferably purified to reduce its ethereal by-product content to a level of not more than 600 ppm.

The invention further resides in a process for preparing polycarbonate which comprises the steps of:
  subjecting a dialkyl oxalate and a phenolic by-product mixture not containing an amine by-product in an amount of more than 600 ppm to transesterification to give a diaryl oxalate, said phenolic by-product mixture having beer obtained by purifying a mixture containing a phenolic by-product and an amine by-product which was collected in a condensation polymerization reaction for preparing polycarbonate from a dialkyl oxalate and a phenolic compound;
  subjecting the diaryl oxalate to decarbonylation to give a diaryl carbonate; and
  reacting the diaryl carbonate with a polyvalent hydroxyl compound in the presence of a catalyst containing an amine compound or an ammonium compound to give the polycarbonate.

In the above-mentioned process, if the phenolic by-product mixture further contains an ethereal by-product, the mixture is preferably purified in advance to reduce its ethereal by-product content to a level of not more than 600 ppm.

BRIEF DESCRIPTION OF THE DRAWING

FIGURE is a schematic flow chart to show a process for preparing a polycarbonate according to the present invention.

DETAILED DESCRIPTION OF THE INVENTION

The process of the invention is further described by referring to the attached drawing.

The steps of the process of the invention are performed continuously in the apparatuses which are connected with lines, as illustrated in the flow chart of the FIGURE in the drawing.

The transesterification performed in the process of the invention includes any reactions in which an alkoxy moiety of the ester compound (i.e., dialkyl oxalate) is exchanged with an phenoxy moiety of the phenolic compound. For instance, the transesterification includes an ordinary transesterification reaction for converting a dialkyl oxalate into an alkyl aryl oxalate and a disproportionation reaction converting the alkyl aryl oxalate into a diaryl oxalate and a dialkyl oxalate.

In the first step, a dialkyl oxalate (particularly, dimethyl oxalate) and a phenolic compound (i.e., phenol or its analogues, particularly, phenol) are subjected to transesterification (including ordinary transesterification reaction and disproportionation reaction) in a liquid phase in the presence of a transesterification catalyst, to give a mixture of reaction products including a diaryl oxalate (particularly, diphenyl oxalate) and a by-produced lower alcohol (particularly, methanol). The diaryl oxalate is separated from the reaction products, purified, and recovered. The by-produced lower alcohol is also separated and recovered.

The dialkyl oxalate is then subjected to a decarbonylation reaction in a liquid phase in the presence of a decarbonylation catalyst, to give a diaryl carbonate (particularly, diphenyl carbonate: DPC) and a by-produced carbon monoxide. The diaryl carbonate is recovered, removing the gaseous carbon monoxide, and purified.

The diaryl carbonate and a polyvalent hydroxyl compound are then subjected to condensation-polymerization reaction in the presence of an appropriate condensation-polymerization catalyst such as an amine compound or an ammonium compound, removing a mixture of by-products such as a phenolic by-product, an amine by-product, and an ethereal by-product, to give polycarbonate.

The mixture of by-products are collected are purified to give a purified phenolic by-product, namely, a pure phenolic compound, which is then employed as a portion or a whole of the phenolic compound in the step for the preparation of a diaryl oxalate.

Examples of the dialkyl oxalates include di-lower-alkyl ester of oxalic acid such as dimethyl oxalate, diethyl oxalate, dipropyl oxalate, dibutyl oxalate, dipentyl oxalate, and dihexyl oxalate. The lower-alkyl preferably contains a straight chain or branched chain alkyl having 1 to 6 carbon atoms, more preferably having 1 to 4 carton atoms. The two alkyl moieties of the dialkyl oxalate may be the same or different from each other.

The dialkyl ester can be produced by a know method. For instance, carbon monoxide (CO) and an alkyl nitrite (represented by the formula of RONO wherein R is a lower alkyl group) are reacted in a gaseous or liquid phase in the presence of a catalyst at a temperature of 10 to 200° C. (particularly 20 to 150° C.) and at a pressure of 2 to 200 atm. (particularly 2 to 100 atm.), to give a dialkyl oxalate (e.g., dimethyl oxalate) and a by-produced nitrogen monoxide (NO). The catalyst comprises a carrier (e.g., active carbon, alumina, spinel, silica, diatomaceous earth, or zeolite) and a platinum metal group catalyst component, such as, a platinum group metal (e.g., platinum met:al or palladium metal), or a salt or complex compound of a platinum group metal, in an amount of 0.01 to 5 wt. % based on the carrier. The alkyl group represented by R in the above-mentioned formula preferably has 1 to 4 carbon atoms, such as methyl, ethyl, n-propyl, isopropyl, n-butyl, or isobutyl. Most preferred is methyl.

The by-produced nitrogen monoxide is, if necessary, reacted with a lower alcohol in the presence of molecular oxygen to produce an alkyl nitrate, which is then utilized in the reaction for preparing a dialkyl oxalate.

As the carbon monoxide to be used for the dialkyl oxalate, a carbon monoxide produced in the decarbonylation step of the process of the invention can be employed.

The phenolic compound to be employed in the first step of the process of the invention is phenol or its analogous compound. The analogous compound is meant to indicate a compound comprising a benzene ring and a hydroxyl group attached to the benzene ring, provided that the hydroxyl group behaves in the same manner as the hydroxyl group of phenol. Therefore, the benzene ring can have one or more substituents. Examples of the substituents include a alkyl group having 1 to 6 carbon atoms (particularly, 1 to 4 carbon atoms), an alkoxy group having 1 to 6 carbon atoms (particularly 1 to 4), and a halogen atom. Preferred phenolic compounds are phenol, a lower alkyl-substituted phenol (e.g., 4-methylphencol, 4-ethylphenol, or 3,4-dimethylphenol). Most preferred is phenol.

In the first step for transesterification, a dialkyl oxalate and a phenolic compound are reacted in a liquid phase at a temperature of approximately 50 to 300° C. (particularly 100 to 250° C.) in the presence of a transesterification catalyst. In this step, a by-produced lower alcohol is continuously removed from the reaction mixture. Thus produced diaryl oxalate is separated from the reaction mixture and purified.

In the first step, an alkyl aryl oxalate is once produced by ordinary transesterification, which is then converted into diaryl oxalate and dialkyl oxalate by a disproportionation reaction. In the step, the dialkyl oxalate is removed to give a diaryl oxalate in an increased yield. The ordinary transesterification is preferably performed at an ordinary or elevated pressure to accelerate the reaction rate, while the disproportionation reaction is preferably performed at a reduced pressure so as to keeping production of by-products low. However, such pressure arrangement may be not necessary.

The first step is preferably performed using a combination of a first reactive distillation column and a second reactive distillation column connected to each other, so that the ordinary transesterification reaction and the disproportionation reaction can be carried out in series. The reactive distillation column preferably has a distillation column having a certain number of column plates (or trays) or packing means. For instance, a reactive distillation column having a theoretical plate number of two or more, particularly 5 to 100, more particularly, 7 to 50, is preferred. Examples of the column plates include a bubble cap tray, a sieve tray, and a bulb tray. The reactive distillation column can be that having a variety of packing means such as Rachig rings, Lessing rings, and pole rings. The reactive distillation column having not only column plates but also packing means can be also employed.

In more detail, the first step can be performed in the following manner.

A dialkyl oxalate, a phenolic compound and a transesterification catalyst are supplied to the first reactive distillation column in which the ordinary transesterification reaction proceeds to mainly yield an alkyl aryl oxalate, while distilling a by-produced gaseous lower alcohol out from the top of the column. The reaction product containing mainly the alkyl alkyl oxalate is taken out from the bottom of the column, and then supplied to the second reactive distillation column.

In the second column, the disproportionation reaction proceeds in the presence of the catalyst to produce a diaryl oxalate, while distilling a by-produced dialkyl oxalate and a mixture containing an amine by-product, and possibly an ethereal by-product, in addition to a phenolic by-product, out of the top of the column. The reaction product mainly comprising a diaryl oxalate is taken out from the bottom of the column. The reaction product is then distilled to recover the target diaryl oxalate, possibly after removing the transesterification catalyst.

The transesterification catalyst preferably is a catalyst soluble in the reaction mixture, such as cadmium compounds, zirconium compounds, lead compounds, iron compounds, compounds of copper or its related metals, zinc compounds, organic tin compounds, Lewis acid compounds of aluminum, Lewis acid compounds of titanium, and Lewis acid compounds of vanadium. More preferred are zirconium compounds, organic tin compound, and Lewis acid compounds of titanium. Most preferred are organic tin compounds, and Lewis acid compounds of titanium.

The ratio of an art of a dialkyl oxalate and an amount of it phenolic compound is chosen depending upon the nature of the catalyst and reaction conditions. Generally, the phenolic compound is employed in an amount of 0.01 to 1,000 moles, preferably 0.1 to 100 moles, more preferably 0.5 to 20 moles, based on one mole of the dialkyl oxalate. The amount of the transesterification catalyst employed in the first step also depends on its nature and the reaction conditions. Generally, the catalyst is employed in an amount of approximately 0.0001 to 50 wt. %, preferably approx. 0.001 to 30 wt. %, based on the total amount of dialkyl oxalate and phenolic compound.

In the second step, the diaryl oxalate produced in the first step is subjected to decarbonylation reaction in the presence of a phosphorus compound catalyst such as an organic phosphorus compound catalyst, to give a reaction product mainly comprising a diaryl carbonate and a by-produced carbon monoxide. The diaryl carbonate is then separated from the reaction product and purified. The gaseous carbon monoxide is removed from the reaction product in the progress of the reaction.

Examples of the phosphorus compound catalysts include phosphine compounds $[P(R^1)(R^2)(R^3)]$, phosphine oxide compounds $[O=P(R^4)(R^5)(R^6)]$, phosphine dihalide compounds $[(Y^1)(Y^2)P(R^7)(R^8)(R^9)]$, and phosphonium salt compounds $[(R^{10})(R^{11})(R^{12})P(R^{13})\cdot X^-]$.

In the above-mentioned formulas, each of $R^1$ through $R^{13}$ represents a substituent group such as a hydrogen atom, an alkyl group having 1 to 16 carbon atoms, an aryl group having 6 to 20 carbon atoms, an aralkyl group having 7 to 25 carbon atoms; X represents an ion or ionic atom group which is capable of forming a counter ion; and each of $Y^1$ and $Y_2$ is a halogen atom (e.g., chloride, bromine, or iodine).

The organic phosphorus compounds of the above-mentioned formulas should have at least one substituent groups other than a hydrogen atom. Preferred are phosphorus compounds in which all of the substituent: groups are aryl groups, particularly, phenyl groups. Also preferred are phosphorus compounds in which one or two of the substituent groups are aryl groups (particularly, phenyl) and other substituent groups are alkyl groups or aralkyl groups.

The organic phosphorus compound can be employed in combination with other compounds to form the decarbonylation catalyst.

In the second step, the diaryl oxalate and the organic phosphorus compound catalyst, if appropriate, are supplied to a decarbonylation vessel, in which the decarbonylation reaction proceeds at a temperature of 100 to 450° C. (preferably 160 to 400° C., more preferably 180 to 350° C.) and a pressure of 10 mmHg to 10 kg/cm², while a by-produced gaseous carbon monoxide is removed, give a diaryl carbonate.

There are no specific limitations with respect to the types of decarbonylation vessel for the second step, provided that the above-mentioned decarbonylation reaction can proceed in the vessel. For instance, a complete mixing reactor (or stirring vessel), a tube reactor comprising heat-exchangeable multiple pipes, and a column or tower type reactor can be employed.

The reaction mixture produced by the decarbonylation reaction contains an unreacted diaryl oxalate and the decarbonylation catalyst in addition to the desired diaryl carbonate. Then, the diaryl carbonate is preferably recovered from the reaction mixture by, first, separating the catalyst out in a distilling apparatus such as a condensation vessel or a thin-layer distilling apparatus, and then distilling the reaction mixture containing no catalyst using an ordinary distilling apparatus such as a packed column or a tray column. The combination of such procedures are favorably employed for obtaining diaryl carbonate of high purity.

The organic phosphorus compounds can be employed singly or in combination to give an appropriate catalyst. The catalyst can be homogeneously dissolved and/or suspended in the reaction solution. In the second step, the organic phosphorus compound catalyst is preferably employed in the range of 0.001 to 50 mol. %, particularly 0.01 to 20 mol. %, based on the molar amount of the diaryl oxalate.

In the third step, the diaryl carbonate obtained in the second step and a polyvalent hydroxyl compound are subjected to condensation-polymerization reaction, removing a mixture of a phenolic by-product and other by-products, to give the desired polycarbonate. The polyvalent hydroxyl compound preferably is an aromatic polyvalent hydroxyl compound in which plural number (particularly, two) of hydroxyl groups are directly attached to an aromatic ring of an aromatic compound. Preferred are divalent aromatic hydroxyl compounds or mixture containing a divalent aromatic hydroxyl compound in an amount of 60 mol. % or more, particularly 80 mol. % or more.

Examples of the polyvalent hydroxyl compounds include bis(hydroxyaryl)alkanes such as bis(4-hydroxyphenyl) methane, 1,1-bis(4-hydroxyphenyl)ethane, 2,2-bis(4-hydroxyphenyl)propane, 2,2-bis(4-hydroxyphenyl)-butane, and 2,2-bis(4-hydroxy-2-methylphenyl)propane, and dihydroxydiaryl ethers such as 4,4'-dihydroxydiphenyl ether and 4,4'-dihydroxy-3,3'-dimethyldiphenyl ether. Preferred is 2,2-bis(4-hydroxyphenyl)propane or a mixture containing 2,2-bis(4-hydroxyphenyl)propane in an amount of not less than 80 mol. %.

Examples of the diaryl carbonates include diphenyl carbonate, ditolyl carbonate, di(p-chlorophenyl) carbonate, and di(m-cresyl) carbonate. Preferred are diaryl carbonate containing 13 to 20 carbon atoms. Most preferred is diphenyl carbonate.

In the third step, the diaryl carbonate is preferably employed in an amount of 1.001 to. 1.5 moles, particularly 1.01 to 1.3 moles, per one mole of the polyvalent hydroxyl compound (particularly, a divalent aromatic hydroxyl compound). In the reaction of the third step, an appropriate polymerization-regulating agent, a terminal group-modifying agent, and/or a monophenol compound can be utilized in addition to the combination of a diaryl carbonate and a polyvalent hydroxyl compound.

The third step is preferably carried out by reacting a diaryl carbonate and a polyvalent hydroxyl compound in the presence of a condensation-polymerization catalyst containing an appropriate amine compound or ammonium compound at a temperature of approximately 80 to 350° C., removing a by-product mixture mainly comprising a phenolic by-product. It is preferred that the reaction temperature is increased and the reaction pressure is reduced, as the reaction advances, so as to produce the desired polycarbonate by one step or plural steps.

The condensation-polymerization catalyst preferably is a base catalyst containing an ammonium compound such as a tetra-substituted ammonium hydroxide having alkyl, aryl or aralkyl substituents, or an amine compound having an alkyl, aryl or aralkyl substituent. Examples of the condensation-polymerization catalysts include those comprising an organic acid salt, inorganic acid salt, hydroxide, hydride, or alcoholate of an alkali metal or alkaline earth metal and a amine or ammonium compound in combination. Preferred are a combination of an alkali metal catalyst component (an inorganic acid salt, an organic acid salt, hydroxide, hydride, or alcoholate of an alkali metal) and an amine or ammonium compound.

The catalyst is preferably employed in an amount of $10^{-5}$ to $10^{-4}$ mol., per one mole of the polyvalent hydroxyl compound. The alkali metal or alkaline earth metal catalyst component is preferably employed in an amount of $10^{-7}$ to $10^{-4}$ mol., per one mole of the polyvalent hydroxyl compound, while the amine or ammonium compound is preferably employed in an amount of $10^{-5}$ to $10^{-4}$ mol., per one mole of the polyvalent hydroxyl compound.

The condensation polymerization reaction of the third step can be performed in the same manner (particularly a melted condensation-polymerization reaction) as that conventionally employed in the known proceeds for the preparation of polycarbonate. For instance, the condensation-polymerization reaction is initially carried out at a temperature of 80 to 240° C., at an atmospheric pressure or reduced pressure for 0.01 to 5 hours, and then the reaction is carried out at an increased temperature (e.g., 240 to 320° C.) and a more reduced pressure (so as to finally reach a pressure of 1 mmHg or less).

Examples of the amine compounds include tertiary amines such as trimethylamine, trimethylamine, dimethylbenzylamine, methyldiphenylamine, and triphenylamine; secondary amines such as dimethylamine, diethylamine, methylbenzylamine; and primary amines such as methylamine, ethylamine, benzylamine, and phenylamine. Preferred are tertiary amines having 1 to 3 (particularly. 1 to 2) carbon atoms, such as trialkylamine.

Examples of the ammonium compounds include ammonium hydroxides having alkyl, aryl, and/or aralkyl group (e.g., tetra substituted ammonium hydroxides such as tetramethylammonium hydroxide, tetramethylammonium hydroxide, tetrabutylammonium hydroxide, and trimethylphenylammonium hydroxide) and tetra-substituted ammonium borohydrides (e.g., tetramethylammnoium borohydride, and tetrabutylammonium borohydride). Preferred are tetra-N-alkyl substituted ammonium hydroxide having 1 to 3 (particularly 1 to 2) carbon atoms.

In the condensation-polymerization catalyst, the amine or ammonium compound is preferably employed in combination with an alkali metal or alkaline earth metal catalyst component.

Examples of the alkali metal catalyst components include alkali metal hydroxides such as sodium hydroxide, potassium hydroxide, and lithium hydroxide; alkali metal inorganic acid salts such as sodium hydrogen carbonate, sodium hydrogen potassium, lithium hydrogen carbonate, sodium carbonate, potassium carbonate, lithium carbonate, sodium dihydrogen phosphate, potassium dihydrogen phosphate, lithium dihydrogen phosphate, sodium dihydrogen phosphite, potassium dihydrogen phosphite, dipotassium hydrogen phosphate, and dilithium hydrogen phosphate; and alkali metal organic acid salts such as sodium acetate, potassium acetate, lithium acetate, sodium stearate, and sodium benzoate.

Examples of the alkaline earth metal catalyst components are salts of magnesium, calcium, and barium and hydroxides, such as those mentioned above.

The condensation-polymerization reaction can be carried out continuously or by a batch system. The reaction apparatus can be a vessel-type reactor or a tube reactor (a self-cleaning reactor is preferred, particularly for performing the second high-temperature, reduced-pressure reaction). A column-type reactor can be also employed.

The by-product mixture comprising an amine compound (by-product) in addition to the phenolic compound (by-product) which is removed in the third step is (collected. The by-product mixture is then purified until the content of the amine by-product is decreased to a level of 600 ppm or less (preferably 500 ppm or less, particularly 100 ppm or less, generally not less than 0.02 ppm). It is not practically advantageous to reduce the amount of amine by-product to a level of 0.02 ppm or less. The amount of the amine by-product is calculated on the basis of the amount of purified phenolic by-product.

If the by-product mixture further contains an ethereal by-product, the by-product mixture is preferably purified until the content of the ethereal by-product is also decreased to a level of 600 ppm or less (preferably 500 ppm or less, particularly 100 ppm or less, generally not less than 0.02 ppm). It is not practically advantageous to reduce the amount of ethereal by-product to a level of 0.02 ppm or less. The amount of the ethereal by-product is calculated on the basis of the amount of purified phenolic by-product.

The purification is preferably performed using a conventionally employed distilling apparatus such as a distilling apparatus using packing means or a distillation column using column plates (or trays). Particularly, if the by-product mixture essentially comprises a phenolic by-product and other by-products having a boiling point lower than the that of the phenolic by-product, the lower boiling point by-products are removed from the top of the distilling apparatus, while the purified phenolic by-product of high purity is taken out from the bottom or the side position (namely, side-cut). If the by-product mixture essentially comprises a phenolic by-product and other by-products having a boiling point higher than the that of the phenolic by-product, the phenolic by-product is taken out from the top of the distilling apparatus, while the higher boiling point by-products are removed from the bottom of the distilling apparatus at an appropriate time. If a lower boiling point by-product and a higher boiling point by-product is contained in the phenolic by-product mixture, the former by-product is removed from the top and the latter by-product is removed from the bottom, and the purified phenolic by-product is preferably taken out front the side portion of the distilling apparatus, particularly in the case that the reaction is conducted continuously.

The amine by-products may be tri-substituted tertiary amines having the formula of $R_3N$ (R is alkyl, aryl, or aralkyl), such as trimethylamine, trimethylamine, dimethylphenylamine, triphenylamine, dimethylbenzylamine, and trimethylbenzylamine. If the condensation-polymerization catalyst contains trialkylamine or tetra-N-alkyl substituted ammonium hydroxide, the amine by-product generally comprises a tri-substituted amine compound having a boiling point lower than that of the phenolic by-product (such as phenol).

In the condensation-polymerization reaction, the phenolic by-product mixture may further contain ethereal by-products such as anisole and phenyl ether. Such ethereal by-products are preferably removed. The ethereal by-products per se are considered generally not to disturb the first transesterification reaction when the purified phenolic by-product is employed in the reaction. However, if the ethereal by-products are accumulated in the reaction system of the first step, the transesterification may be disturbed, particularly in the case that dimethyl oxalate is employed as the starting dialkyl oxalate.

For instance, anisole and dimethyl oxalate have a boiling point similar to each other. Accordingly, when the dimethyl oxalate is repeatedly employed in the transesterification reaction by means of a recycling system, the separation of dimethyl oxalate from anisole is not easily carried out, and the recycling system is not smoothly operated.

If the ethereal by-products comprise diphenyl ether, phenyl butyl ether and/or phenethol which may be by-produced in the condensation-polymerization reaction, they may be accumulated in the transesterification reaction system, because these ethereal by-products have a boiling point between that of the starting dialkyl oxalate and that of the produced diaryl oxalate and therefore it is not easy to sharply separate the ethereal by-products from the transesterification reaction system.

Representative ethereal by-products are phenyl ether compounds having the formula of ArOR (Ar is an aryl group, typically phenyl group, possibly having a substituent group and R is alkyl, aryl or aralkyl) such as alkyl phenyl ethers (e.g., anisole, ethyl phenyl ether, propyl phenyl ether, and butyl phenyl ether); diaryl ethers (e.g., diphenyl ether, methylphenyl phenyl ether, and phenoxyphenol); benzyl phenyl ether; and dimethylbenzyl ether.

The ethereal by-products are removed simultaneously when the amine by-products are removed to purify the phenolic by-product mixture.

The purified phenolic by-product can be employed as a whole or a portion (approximately 20 wt. % or more, particularly 50 to 90 wt. % of the phenolic compound for the first step, namely, the step for transesterification. The purified phenolic by-product can be supplied to the first step using appropriate supplying systems. The supply system can comprise a storage tank, a pumping system, and a tube line connected to the apparatus for performing the transesterification reaction. It is preferred that the purifies phenolic by-product is intermittently or continuously supplied to the reactor for the transesterification reaction (e.g. reactive distillation column), so that the purified phenolic by-product is employed in the recycling system.

The process for the preparation of polycarbonate according to the present invention is capable of producing almost colorless polycarbonate having a high molecular weight such as in the range of approximately 10,000 to 80,000, particularly 15,000 to 60,000.

EXAMPLE 1

(1) Transesterication (Preparation of Diphenyl Oxalate)
Diphenyl oxalate (DPO: diphenyl oxalate) was produced from dimethyl oxalate (DMO: dimethyl oxalate) and phenol (PhOH) by the following procedures.

Into a first reactive distillation column (inner diameter: 32 mm, 50 column plates, named "Oldershaw column") equipped with a 1-L volume bottom flask was introduced a mixture of 54.1 wt. % of phenol, 45.3 wt. of dimethyl oxalate, and 0.5 wt. % of tetraphenoxytitanium (TPT) at the 12th (from the top) column plate at a feed rate of 600 mL/h. Simultaneously, the bottom flask was heated on a mantle heater to 190° C. The ordinary transesterification reaction was carried out at a reflux ratio of 2, taking a produced vapor out from the top. The reflux was conducted with condensing a portion of the produced vapor using a condenser.

When the conditions in the first reactive distillation column became stable (approximately at a lapse of 4 hours from the beginning of the supply of the reactant mixture), the reaction mixture at the bottom had the following composition:

| | |
|---|---|
| diphenyl oxalate | 6.23 wt. % |
| methyl phenyl oxalate (MPO) | 29.95 wt. % |
| dimethyl oxalate | 23.88 wt. % |
| phenol | 39.41 wt. %. |

The vapor taken out from the top at that time had the following composition:

| | |
|---|---|
| methanol | 99.7 wt. % |
| dimethyl oxalate | 0.3 wt. % |
| amount (taking-out rate) | approx. 44 g/h |

The reaction mixture taken out from the bottom of the first reactive distillation column was then introduced into a second reactive distillation column. (Oldershaw column) of the same structure at the 12th (from the top) column plate at a reduced pressure (200 mmHg) at a feed rate o)f 600 mL/h. Simultaneously, the bottom flask was heated on a mantle heater to 200° C. The disproportionation reaction was carried out with no refluxing, taking a produced vapor out from the top using a condenser.

When the conditions in the second reactive distillation column became stable (approximately at a lapse of 4 hours from she beginning of the supply of the reactant), the reaction mixture taken out from the bottom (at a rate of approx. 268 g/h) had the following composition:

| | |
|---|---|
| diphenyl oxalate | 65.27 wt. % |
| methyl phenyl oxalate (MPO) | 18.43 wt. % |
| dimethyl oxalate | 1.02 wt. % |
| phenol | 13.93 wt. %. |

The vapor taken out from the top at that time had the following composition:

| | |
|---|---|
| methanol | 1.57 wt. % |
| dimethyl oxalate | 46.53 wt. % |
| phenol | 48.51 wt. % |
| methyl phenyl oxalate | 2.97 wt. % |
| diphenyl oxalate | 0.42 wt. % |
| amount (taking-out rate) | approx. 371 g/h |

The reaction mixture taken out from the bottom was placed in a rotary thin-layer distillation apparatus (heat conductive area: 0.1 m$^2$) at a feed rate of 200 mL/h. The inner pressure of the apparatus was reduced to 15 mmHg, and the apparatus was heated to 200° C. by means of a heat medium, so that dimethyl oxalate, phenol, and methyl phenyl oxalate were continuously evaporated. The vapor was then fed to a distillation column (inner diameter: 30 mm, length: 2 m) at the position of 80 cm (from the top), and distillation was carried out continuously.

From the top of the distillation column, a condenses liquid comprising 3.05 wt. % of dimethyl oxalate, 41.73 wt. % of phenol, and 55.21 wt. % of methyl phenyl oxalate was taken out at approximately 68 mL/h. Simultaneously, the reaction mixture was taken out from the bottom at a rate of approximately 120 g/h. The reaction mixture was then distilled in a distillation apparatus of the same type (glass column, 30 mmφ×2 m, 5×5 mm Helipack) to obtain diphenyl oxalate of 99.95% purity containing 0.02 wt. % of phenol and 0.01 wt. % of methyl phenyl oxalate at a yield of approximately 120 g/h. From the bottom of the distillation apparatus, a reaction liquid containing approx 1.1 wt. % (as a titanium metal) of titanium compound was taken out at a rate of approx. 23 g/h.

(2) Decarbonylation (Preparation of Diphenyl Carbonate)

The diphenyl oxalate obtained in the above-mentioned reaction was processed in the below-mentioned manner to give diphenyl carbonate (DPC).

To the diphenyl carbonate was added 1 mol. % of tetraphenylphosphonium chloride, and the mixture was heated to 150° C. whereby a solution was obtained. The resulting solution was fed into one of two 1-L volume glass reactors connected in series at a feed rate of 300 mL/h using a quantitatively supply pump. The reactors were equipped with a thermometer, a stirrer, and an over-flow pipe. Simultaneously, the reactors were heated on mantle heaters to keep a temperature of 230° C., whereby proceeding decarbonylation of diphenyl oxalate.

The over-flow position for each reactor was set at 600 mL. The over-flown reaction mixture taken cut (at a rate of approx. 270 mL/h) at a lapse of 20 hours; from the beginning of the supply of the reactant had the following composition:

| | |
|---|---|
| diphenyl oxalate | 14.6 wt. % |
| diphenyl carbonate | 84.0 wt. % |
| phenol | 0.08 wt. %. |

A gaseous product taken out from each reactor comprised approx. 100% of carbon monoxide. The total amount of the collected carbon monoxide was 25 liters (standard condition)/h.

The reaction liquid obtained after the decarbonylation reaction was fed onto a rotary thin-layer distillation apparatus of the aforementioned structure (made of glass, moving part: made of Hastelloy CR) at a feed rate of 250 mL/h at a reduced pressure of 20 mmHg. Simultaneously, the distillation apparatus was heated to 200° C. using a heat medium, whereby tetraphenylphosphonium chloride was separated out. The distillate taken out from the apparatus (92.2 wt. % of diphenyl carbonate and 7.7 wt. % of diphenyl oxalate) was continuously introduced into a glass-made distillation column (same as that used for separation and purification in the transesterification step), whereby continuous distillation was carried out (pressure at the top: 20 torr, reflux ratio: 5), to obtain diphenyl carbonate of 99.9% purity at a rate of approximately 220 mL/h.

(3) Condensation-polymerization (Preparation of Polycarbonate)

From a mixture of 800 mL of toluene and 36 mL of ethanol (volume ratio: 22/1) was recrystallized 400 g of bisphenol A to give a bisphenol A of high purity.

In a 100 mL-volume reactor (made of stainless steel SUS 316L) were placed 22.85 g (1 mol.) of the purified bisphenol A, 22.68 g (0.106 mol.) of diphenyl carbonate obtained above, and a catalyst (20 mg of sodium dihydrogen phosphate and 5 mg of tetramethylammonium hydroxide). The inner space of the reactor was made to vacuum at room temperature for 0.5 hour, and into the inner space was supplied a nitrogen gas to reach an atmospheric pressure in the inner space. The reactor was then heated for conducting the condensation-polymerization reaction.

In the procedure of condensation-polymerization reaction, the reaction mixture was heated at 200° C. for 10 minutes and then at 230° C. for 10 minutes. Subsequently, the pressure of the inner space was reduced gradually at 230° C. When the pressure reached 200 mmHg at 230° C., phenol began to be taken out, and the condition was kept for one hour. The reaction mixture in the reactor was further heated at 240° C. and at 100 mmHg for 0.5 hour. The reaction mixture was further heated at 255° C. and at 100 mmHg for 10 minutes. Subsequently, the pressure of the inner space was reduced from 100 m to 50 =mmHg for a period of 15 minutes. Under such conditions, the reaction was continued for 15 minutes. Subsequently, the pressure of the inner space was reduced from 50 mmHg to 0.1 mgHG at 270° C. for a period of 30 minutes. Under such conditions, the reaction was continued for 1 hour.

Thus, 25.43 g (yield: 100%) of polycarbonate was obtained.

The obtained polycarbonate had a logarithmic viscosity (measured at 0.5 g/100 mL (30%), solvent: chloroform) of 0.497 dl/g and a weight average mean molecular weight (calculated as that of polystyrene) of 53,000. The polycarbonate was almost non-colorless and transparent by visual observation).

After the condensation-polymerization reaction, 17.6 mL (total amount) of a phenolic by-product mixture was collected. The mixture was analyzed by gas chromatography, and confirmed that 150 ppm of trimethylamine and 280 ppm of anisole were contained.

The phenolic by-product mixture was distilled in the glass distillation apparatus (the same as that used in the decarbonylation reaction) at a reduced pressure of 200 mmHg and at a reflux ratio of 2. The initial 3% of the distillate taken out at the top was removed. Thus, a purified phenolic by-product containing 2 ppm of trimethylamine and 5 ppm of anisole was obtained.

Thus purified phenolic by-product was supplied to the first reactive distillation column for the transesterification reaction and employed in place of fresh phenol for carrying out the same transesterification reaction. The result was the same as that obtained in the use of fresh phenol as the starting compound.

EXAMPLE 2

A feed liquid containing 54.1 wt. % of phenol, 45.3 wt. % of DMO, 0.5 wt. % of TPT and 270 ppm of trimethylamine was employed for performing transesterification reaction to produce diphenyl oxalate in the same manner as in Example 1. The content of 270 ppm of trimethylamine corresponded to 555 ppm on the phenol content base.

When the conditions of the first reactive distillation column became stable (at a lapse of 4 hours starting from the supply of the starting compounds), the reaction mixture taken from the bottom (taking-out rate: approx. 608 g/h) had the following composition:

| | |
|---|---|
| diphenyl oxalate | 6.05 wt. % |
| methyl phenyl oxalate | 27.21 wt. % |
| dimethyl oxalate | 25.07 wt. % |
| phenol | 41.13 wt. %. |

The vapor taken out from the top at that time had the following composition:

| | |
|---|---|
| methanol | 99.7 wt. % |
| dimethyl oxalate | 0.3 wt. % |
| amount (taking-out rate) | approx. 39 g/h |

EXAMPLES 3 to 6

The procedures of Example 2 were repeated except that the nature and amount of the impurity (amine compound) was varied as indicated below. In the case that triethylamine was employed as the amine impurity, the decarbonylation reaction was carried out using tetraethylammonium hydroxide in place of tetramethylammnium hydroxide.

The results are set forth below.

EXAMPLE 3

Amine compound: trimethylamine
Amine concentration in phenol: 100 ppm
Composition of reaction mixture at bottom
  DMO: 24.12 wt. %, PhOH: 40.28 wt. %,
  MPO: 28.93 wt. %, DPO: 6.11 wt. %
Taking-out rate (from bottom): 605 g/h
Composition of vapor taken out from top
  MeOH: 99.7 wt.1, DMO; 0.3 wt. %
Taking-out rate (from top): 42 g/h

EXAMPLE 4

Amine compound: trimethylamine
Amine concentration in phenol: 5 ppm
Composition of reaction mixture at bottom
  DMO: 23.89 wt. %, PhOH: 39.48 wt. %,
  MPO: 29.93 wt. %, DPO: 6.21 wt. %
Taking-out rate (from bottom): 603 g/h
Composition of vapor taken out from top
  MeOH: 99.7 wt. %, DMO: 0.3 wt. %
Taking-out rate (from top): 44 g/h

EXAMPLE 5

Amine compound: trimethylamine
Amine concentration in phenol: 500 ppm
Composition of reaction mixture at bottom
  DMO: 25.10 wt. %, PhOH: 41.09 wt. %,
  MPO: 27.18 wt. %, DPO: 6.02 wt. %
Taking-out rate (from bottom): 608 g/h
Composition of vapor taken out from top
  MeOH: 99.7 wt. %, DMO: 0.3 wt. %
Taking-out rate (from top): 39 g/h

EXAMPLE 6

Amine compound: triphenylamine
Amine concentration in phenol: 500 ppm
Composition of reaction mixture at bottom
  DMO: 24.98 wt. %, PhOH: 40.76 wt. %,
  MPO: 27.64 wt. %, DPO: 6.08 wt. %
Taking-out rate (from bottom): 607 g/h Composition of vapor taken out from top
  MeOH: 99.7 wt. %, DMO: 0.3 wt. %
Taking-out rate (from top): 40 g/h.

COMPARISON EXAMPLE 1

A feed liquid containing 54.1 wt. % of phenol, 45.3 wt. % of DMO, 0.5 wt. % of TPT and 1,000 ppm of trimethylamine was employed for performing transesterification reaction to produce diphenyl oxalate in the same manner as in Example 1. The content of 1,000 ppm of triethylamine corresponded to 2,000 ppm on the phenol content base.

When the conditions of the first reactive distillation column became stable (at a lapse of 4 hours starting from the supply of the starting compounds), the reaction mixture taken from the bottom (taking-out rate: approx. 613 g/h) has the following composition:

| | |
|---|---|
| diphenyl oxalate | 4.21 wt. % |
| methyl phenyl oxalate | 23.42 wt. % |
| dimethyl oxalate | 28.43 wt. % |
| phenol | 43.39 wt. %. |

The vapor taken out from the top at that time had the following composition:

| | |
|---|---|
| methanol | 99.7 wt. % |
| dimethyl oxalate | 0.3 wt. % |
| amount (taking-out rate) | approx. 34 g/h. |

COMPARISON EXAMPLE 2

A feed liquid containing 54.1 wt. % of phenol, 45.3 wt. % of DMO, 0.5 wt. % of TPT and 350 ppm of trimethylamine was employed for performing transesterification reaction to produce diphenyl oxalate in the same manner as in Example 1. The content of 350 ppm of triethylamine corresponded to 700 ppm on the phenol content base.

When the conditions of the first reactive distillation column became stable (at a lapse of 4 hours starting from the supply of the starting compounds), the reaction mixture taken from the bottom (taking-out rate: approx. 612 g/h) had the following composition:

| | |
|---|---|
| diphenyl oxalate | 4.21 wt. % |
| methyl phenyl oxalate | 23.82 wt. % |
| dimethyl oxalate | 28.30 wt. % |
| phenol | 43.10 wt. %. |

The vapor taken out from the top at that time had the following composition:

| | |
|---|---|
| methanol | 99.7 wt. % |
| dimethyl oxalate | 0.3 wt. % |
| amount (taking-out rate) | approx. 35 g/h. |

EXAMPLE 7

The procedures of Example 1 were repeated except that the first reactive distillation column and the second reactive distillation column were connected in series for forming continuous recycling system.

Into the first reactive distillation column (inner diameter: 32 mm, 50 column plates named "Oldershaw column") equipped with a 1-L volume bottom flask w;3s introduced a mixture of 54.1 wt. % of phenol, 45.3 wt. % of dimethyl oxalate, and 0.5 wt. of tetraphenoxytitanium (TPT) at the 12th (from the top) column plate at a feed rate of 600 mL/h. Simultaneously, the bottom flask was heated on a mantle heater to 190° C. The ordinary transesterification reaction was carried out at a reflux ratio of 2, taking a produced vapor out from the top. The reflux was conducted with condensing a portion of the produced vapor using a condenser.

When the conditions in the first reactive distillation column became stable (approximately at a lapse of 4 hours from the beginning of the supply of the reactant mixture), the reaction mixture taken out from the bottom (taking-out rate: approx. 603 g/h) had the following composition:

| | |
|---|---|
| diphenyl oxalate | 6.19 wt. % |
| methyl phenyl oxalate (MPO) | 30.02 wt. % |
| dimethyl oxalate | 25.74 wt. % |
| phenol | 37.38 wt. %. |

The vapor taken out from the top at that time had the following composition:

| | |
|---|---|
| methanol | 99.7 wt. % |
| dimethyl oxalate | 0.3 wt. % |
| amount (taking-out rate) | approx. 44 g/h |

The reaction mixture taken out from the bottom of the first reactive distillation column was then introduced into the second reactive distillation column (Oldershaw column) at the 12th (from the top) column plate at a reduced pressure (200 mmHg) at a feed rate of 603 mL/h. Simultaneously, the bottom flask was heated on a mantle heater to 200° C. The disproportionation reaction was carried out with no refluxing, taking a produced vapor out from the top using a condenser.

When the conditions in the second reactive distillation column became stable (approximately at a lapse of 4 hours from the beginning of the supply of the reactant), the reaction mixture taken out from the bottom fiat a rate of approx. 213 g/h) had the following composition:

| | |
|---|---|
| diphenyl oxalate | 65.13 wt. % |
| methyl phenyl oxalate | 18.39 wt. % |
| dimethyl oxalate | 1.21 wt. % |
| phenol | 13.18 wt. %. |

The vapor taken out from the top at that time had the following composition:

| | |
|---|---|
| methanol | 1.57 wt. % |
| dimethyl oxalate | 41.81 wt. % |
| phenol | 53.23 wt. % |
| methyl phenyl oxalate | 2.95 wt. % |
| diphenyl oxalate | 0.43 wt. % |
| amount (taking-out rate) | approx. 390 g/h |

The vaper taken out from the top of the second reactive distillation column and condensed was once placed in a3-L volume glass vessel. Subsequently, the condensed vapor was fed into the first reactive distillation column at a rate corresponding to that taken out from the second column (approx. 390 g/h) at the same 12th column plate. Thus, a recycling system was formed.

When the recycling system was initiated, the amounts of the fresh starting compounds employed in the case adopting no recycling system were reduced so that the total amount of the recycled starting compounds and the fresh starting compounds could correspond to the initially set amount, that is, DMO45.3 wt. %, phenol 54.1 wt. %, and TPT 0.5 wt. %, feed rate: approximately 600 mL/h.

The reaction mixture taken out from the bottom of the second reactive distillation column was placed in a rotary thin-layer distillation apparatus (heat conductive area: 0.1 m$^2$) at a feed rate of 200 mL/h. The inner pressure of the apparatus was reduced to 15 mmHg, and the apparatus was heated to 200° C. by means of a heat medium, so that diethyl oxalate, phenol, and methyl phenyl oxalate were continuously evaporated. The vapor was then fed to a distillation apparatus (inner diameter: 30 mm, length: 2 m, packing means: 5×5mm Helipack, MPO recovering column) at the position of 80 cm (from the lop), and distillation was carried out continuously.

From the top of the distillation column, a condensed liquid comprising 3.05 wt. % of dimethyl oxalate, 41.73 wt. % of phenol, and 55.21 wt. % of methyl phenyl oxalate was taken out at approximately 68 mL/h. Simultaneously, the reaction mixture was taken out from the bottom at a rate of approximately 120 g/h. The reaction mixture was once placed in a 3L-volume glass vessel. Subsequently, the reaction mixture was continuously fed into the second reactive distillation column at a rate corresponding to that taken out from the second column at the 30th column plate (from the top).

The reaction mixture taken out from the bottom was distilled in a distillation apparatus (same as the MPO recovering column), to give diphenyl oxalate of 99.95 wt. % purity containing 0.02 wt. % of phenol and 0.01 wt. % of methyl phenyl oxalate at a rate of approx. 120 g/h.

From the bottom of the distillation apparatus, a reaction liquid containing approx. 1.1 wt. % (as a titanium metal) of titanium compound was taken out at a rate of approx. 23 g/h., and recycled into the first reactive distillation column at the starting compound feeding position.

The decarbonylation reaction and the condensation-polymerization reaction were then performed. The collected phenolic by-product mixture was purified to give a phenolic by-product mixture containing 2 ppm of trimethylamine and 5 ppm of anisole) and fed to the first reactive distillation column of the first step.

In the course of transesterification reaction and disproportionation reaction, a small amount of high boiling point by-products were produced. A portion of the recovered catalyst-containing liquid was removed so that the amount of impurities in the liquid could not exceed 50 wt. % Then a portio of the liquid was removed, a fresh catalyst was added in such an amount to compensate the removed amount.

The above-described recycling system was operated continuously for 100 hours. The reaction rate and the compositions of the reaction mixtures taken out at various positions were kept constant, to give the target diphenyl oxalate.

COMPARISON EXAMPLE 2

The procedures of Example 7 were repeated using a feed liquid containing 1,000 ppm of anisole, to produce diphenyl oxalate.

In the first reactive distillation column, anisole was deposited at the upper portion of the column when the reaction was performed under the same conditions as those of Example 7. Therefore, the reflux condition was changed to remove all anisole together with methanol. The methanol recovered from the top contained 0.25 wt. % of anisole and 0.63 wt. % of dimethyl oxalate.

COMPARISON EXAMPLE 3

The procedures of Example 7 were repeated using a feed liquid containing 1,000 ppm of diphenyl ether, to produce diphenyl oxalate.

In the recycling system using the above feed liquid, the amount of diphenyl oxalate in the vapor (phenol/DMO) recovered from the top of MPO recovering column increased gradually to reach 2.7 wt. % at a lapse of 100 hours. The recycling system was further continued for 100 hours, and the content of diphenyl oxalate reached 5.4 wt. %.

In the course of increasing the amount of diphenyl oxalate in the vapor, the reaction rate in the first reactive distillation column decreased. Further, the operating conditions varied not only in the first reactive distillation column but also in the second reactive distillation column, the evaporator, and the MPO recovering column.

What is claimed is:

1. A process for preparing polycarbonate which comprises the steps of:
    subjecting a dialkyl oxalate and a phenolic compound to transesterification to give a diaryl oxalate;
    subjecting the diaryl oxalate to decarbonylation to give a diaryl carbonate;
    reacting the diaryl carbonate with a polyvalent hydroxyl compound in the presence of a catalyst containing a tertiary amine having $C_1$–$C_3$ alkyl group or a tetra-N-alkyl substituted ammonium hydroxide having $C_1$–$C_3$ alkyl group to give a polycarbonate, removing a mixture containing a phenolic by-product and an amine by-product that has a boiling point lower than that of the phenolic by-product;
    collecting the mixture;
    purifying the mixture so that the amount of the amine by-product in the mixture is reduced to give a phenolic by-product mixture not containing the amine by-product in an amount of more than 600 ppm; and
    utilizing thus purified phenolic by-product mixture as a whole or a part of the phenolic compound in the first step.

2. The process of claim 1, wherein the catalyst further contains an alkali metal or an alkaline earth metal.

3. The process of claim 1, wherein each of the phenolic compound and the phenolic by-product consists essentially of phenol.

4. The process of claim 1, wherein the step of purifying the mixture is performed by distilling off the amine by-product from the mixture.

5. The process of claim 1, wherein the step of purifying the mixture is performed in such manner that the amount of the amine by-product in the mixture is reduced to give a phenolic by-product mixture not containing the amine by-product in an amount of more than 100 ppm.

6. A process for preparing polycarbonate which comprises the steps of:
    subjecting a dialkyl oxalate and a phenolic by-product mixture not containing an amine by-product in an amount of more than 600 ppm to transesterification to give a diaryl oxalate, said phenolic by-product mixture having been obtained by purifying a mixture containing a phenolic by-product and an amine by-product that has a boiling point lower than that of the phenolic by-product which was collected in a condensation polymerization reaction for preparing polycarbonate from a dialkyl oxalate and a phenolic compound;
    subjecting the diaryl oxalate to decarbonylation to give a diaryl carbonate; and
    reacting the diaryl carbonate with a polyvalent hydroxyl compound in the presence of a catalyst containing a tertiary amine having $C_1$–$C_3$ alkyl group or a tetra-N-alkyl substituted ammonium hydroxide having $C_1$–$C_3$ alkyl group to give the polycarbonate.

7. The process of claim 6, wherein the purified phenolic by-product mixture does not contain the amine by-product in an amount of more than 100 ppm.

8. A process for preparing polycarbonate which comprises the steps of:
    subjecting a dialkyl oxalate and a phenolic compound to transesterification to give a diaryl oxalate;
    subjecting the diaryl oxalate to decarbonylation to give a diaryl carbonate;
    reacting the diaryl carbonate with a polyvalent hydroxyl compound in the presence of a catalyst containing a tertiary amine having $C_1$–$C_3$ alkyl group or a tetra-N-alkyl substituted ammonium hydroxide having $C_1$–$C_3$ alkyl group to give a polycarbonate, removing a mixture containing a phenolic by-product, an amine by-product that has a boiling point lower than that of the phenolic by-product, and an ethereal by-product;
    collecting the mixture;
    purifying the mixture so that the amounts of the amine by-product and etheral product in the mixture is reduced to give a phenolic by-product mixture not containing the amine by-product in an amount of more than 600 ppm and the ethereal by-product in an amount of more than 600 ppm; and
    utilizing thus purified phenolic by-product mixture as a whole or a part of the phenolic compound in the first step.

9. The process of claim 8, wherein the catalyst further contains an alkali metal or an alkaline earth metal.

10. The process of claim 8, wherein each of the phenolic compound and the phenolic by-product consists essentially of phenol.

11. The process of claim 8, wherein the step of purifying the mixture is performed by distilling off the amine by-product from the mixture.

12. The process of claim 8, wherein the step of purifying the mixture is performed in such manner that the amount of the amine by-product in the mixture is reduced to give a phenolic mixture not containing the amine by product in an amount of more than 100 ppm.

* * * * *